United States Patent
Mitsumata et al.

(10) Patent No.: US 10,365,277 B2
(45) Date of Patent: Jul. 30, 2019

(54) METHOD FOR MEASURING HEMAGGLUTININ FROM INFLUENZA VIRUS

(71) Applicant: DENKA SEIKEN CO., LTD., Tokyo (JP)

(72) Inventors: Ryotaro Mitsumata, Gosen (JP); Noriyuki Izutani, Gosen (JP)

(73) Assignee: DENKA SEIKEN CO., LTD., Tokyo (JP)

(*) Notice: Subject to any disclaimer, the term of this patent is extended or adjusted under 35 U.S.C. 154(b) by 0 days.

(21) Appl. No.: 14/432,714

(22) PCT Filed: Oct. 3, 2013

(86) PCT No.: PCT/JP2013/076892
§ 371 (c)(1),
(2) Date: Mar. 31, 2015

(87) PCT Pub. No.: WO2014/054712
PCT Pub. Date: Apr. 10, 2014

(65) Prior Publication Data
US 2015/0233922 A1    Aug. 20, 2015

(30) Foreign Application Priority Data

Oct. 5, 2012 (JP) .................................. 2012-222618

(51) Int. Cl.
*G01N 33/569* (2006.01)

(52) U.S. Cl.
CPC ... *G01N 33/56983* (2013.01); *G01N 2333/11* (2013.01)

(58) Field of Classification Search
None
See application file for complete search history.

(56) References Cited

U.S. PATENT DOCUMENTS

| | | | |
|---|---|---|---|
| 5,612,037 A | 3/1997 | Huebner et al. | |
| 5,631,374 A * | 5/1997 | Novotny | C07D 215/14 436/111 |
| 6,165,710 A | 12/2000 | Robinson | |
| 6,242,582 B1 * | 6/2001 | Reece | C07D 309/28 536/4.1 |
| 2011/0053250 A1 * | 3/2011 | Takakura | C12N 7/00 435/239 |
| 2011/0182940 A1 * | 7/2011 | Takahashi | A61K 39/145 424/210.1 |
| 2012/0065089 A1 | 3/2012 | Kuno et al. | |
| 2012/0171660 A1 * | 7/2012 | Lei | C12N 7/02 435/5 |
| 2012/0172247 A1 | 7/2012 | Narimatsu et al. | |
| 2014/0335507 A1 * | 11/2014 | Dormitzer | G01N 33/56983 435/5 |

FOREIGN PATENT DOCUMENTS

| | | |
|---|---|---|
| CN | 101912602 A * | 12/2010 |
| EP | 1 167 382 A1 | 1/2002 |
| JP | 7-258291 A | 10/1995 |
| JP | 10-503494 A | 3/1998 |
| JP | 2012-185172 A | 9/2012 |
| WO | WO 00/59932 A1 | 10/2000 |
| WO | WO 2010/100862 A1 | 9/2010 |
| WO | WO 2010/136896 A1 | 12/2010 |

OTHER PUBLICATIONS

Opitz et al., Lectin-affinity chromatography for downstream processing of MDCK cell culture derived human influenza A viruses, Vaccine, 25, (2007), p. 939-947.*
Lu et al., A highly specific ELISA for diagnosis of 2009 influenza A (H1N1) virus infections, Journal of the Formosan Medial Association, (2012), 111, p. 693-697.*
CN101912602A English translation of the abstract (1 page) (2010).*
Legastelois et al., "Avian glycan-specific IgM monoclonal antibodies for the detection and quantitation of type A and B haemagglutinins in egg-derived . . . ," Journal of Virological Methods, vol. 178, No. 1-2, Dec. 2011 (E-published Aug. 31, 2011), pp. 129-136, Abstract provided only (1 page).
Mahmood et al., "An ELISA utilizing immobilised snowdrop lectin GNA for the detection of envelope glycoproteins of HIV and SIV," Journal of Immunological Methods, vol. 151, No. 1-2, Jul. 6, 1992, pp. 9-13, Abstract provided only (1 page).
International Search Report, issued in PCT/JP2013/076892, dated Jan. 7, 2014.
Extended European Search Report, dated Apr. 7, 2016, for European Application No. 13844402.1.
Sato et al., "High mannose-specific lectin (KAA-2) from the red alga *Kappaphycus alvarezii* potently inhibits influenza virus infection in a strain-independent manner," Biochemical and Biophysical Research Communications, vol. 405, 2011 (available online Jan. 8, 2011), pp. 291-296.
Xu et al., "Molecular modeling, docking and dynamics simulations of GNA-related lectins for potential prevention of influenza virus (H1N1)," Journal of Molecular Modeling, vol. 18, 2012 (published online Mar. 29, 2011), pp. 27-37.

* cited by examiner

*Primary Examiner* — Bao Thuy L Nguyen
*Assistant Examiner* — Ellen J Marcsisin
(74) *Attorney, Agent, or Firm* — Birch, Stewart, Kolasch & Birch, LLP

(57) ABSTRACT

Disclosed is a novel method for measuring haemagglutinin of an influenza virus, which can construct an assay system in a shorter period of time than a sandwich immunoassay method using two kinds of anti-haemagglutinin antibodies. The method for measuring haemagglutinin of an influenza virus is achieved by a sandwich immunoassay method comprising sandwiching the haemagglutinin between a lectin which binds to the haemagglutinin but does not bind to an antibody, and an anti-haemagglutinin antibody which undergoes antigen-antibody reaction with the haemagglutinin.

8 Claims, 3 Drawing Sheets

A: No treatment

B: Treatment with 1.0% Triton X-100

C: Treatment with 1.0% NP-40

D: Treatment with 1.0% Tween 80

E: Treatment with 1.0% Brij 35

F: Treatment with 1.0% CHAPS

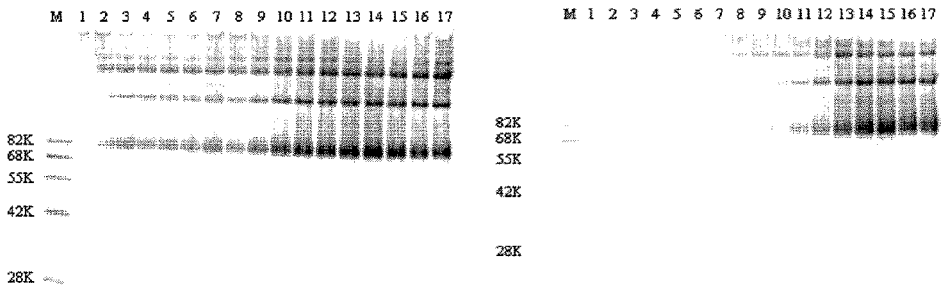
G: Treatment with 1.0% Zwittergent 3-14
H: Treatment with 1.0% CTAB
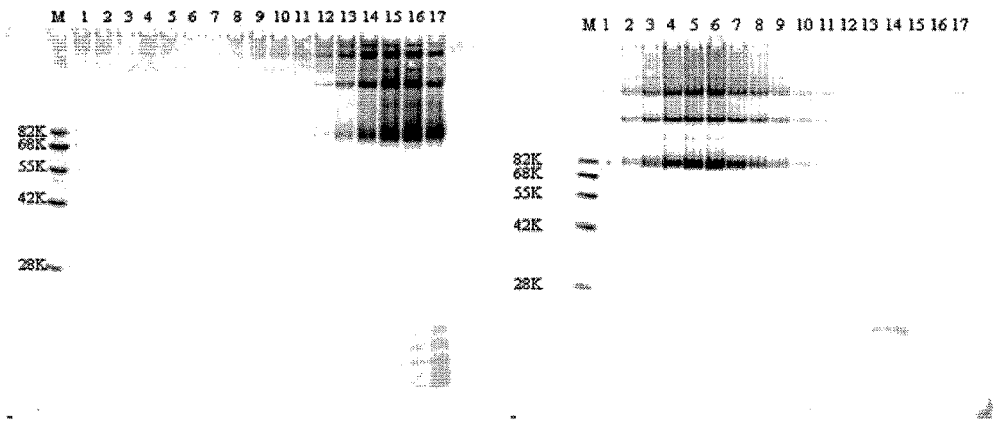
I: Treatment with 0.3% SDS
J: Treatment with 4.0 M Urea
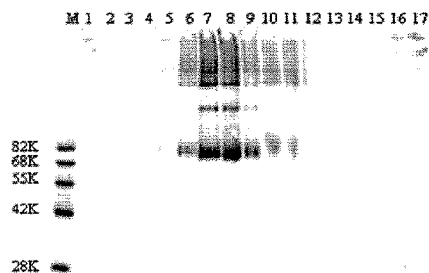
K: Treatment with 3.0 M of Guanidine-Hydrochloride
Fig.1-2

METHOD FOR MEASURING HEMAGGLUTININ FROM INFLUENZA VIRUS

TECHNICAL FIELD

The present invention relates to a method for measuring haemagglutinin which is an antigen of an influenza virus.

BACKGROUND ART

Influenza viruses belong to Orthomyxoviridae and are classified into type A, type B and type C depending on the antigenicity of the nucleoprotein and the matrix protein located in the virus. The type A and type B viruses have been prevalent every year, and in particular, the type A virus is classified into 16 subtypes of haemagglutinin and 9 subtypes of neuraminidase depending on the glycoproteins which are surface antigens on the particles, and undergoes antigenic variation easily.

Therefore, the vaccine strain has to be selected based on the prediction of the prevalence in each season, and it is necessary to prepare a reagent for measuring haemagglutinin which is a main antigen of vaccine in accordance with the change of the strain.

PRIOR ART DOCUMENTS

Non-Patent Documents

[Non-patent Document 1] Mahmood N, Hay A L, "An ELISA utilizing immobilised snowdrop lectin GNA for the detection of envelope glycoproteins of HIV and SIV" J Immunol Methods., 151 (1992) 9-13

[Non-patent Document 2] Legastelois I. et al., "Avian glycan-specific IgM monoclonal antibodies for the detection and quantitation of type A and B haemagglutinins in egg-derived influenza vaccines", J Virol Methods., 178 (2011) 129-136

SUMMARY OF THE INVENTION

Problems to be Solved by the Invention

Although examples of the method for measuring haemagglutinin with high sensitivity and high throughput include a sandwich ELISA using monoclonal antibodies and polyclonal antibodies, two kinds of antibodies specific to the strain are necessary, and it is difficult to provide monoclonal antibodies for measuring haemagglutinin of new vaccine strains or pandemic viruses in view of the period to prepare the antibodies. Further, the measuring method using monoclonal antibodies specific to sugar chains of birds as described in Non-patent Document 2 is not widely used because of the problems in supply and the like due to the unordinary antibody, and the method cannot be used for measuring haemagglutinin of an influenza virus amplified in mammalian cells.

Accordingly, an object of the present invention is to provide a novel method for measuring haemagglutinin of an influenza virus, which can construct an assay system in a shorter period of time than a sandwich immunoassay method using two kinds of anti-haemagglutinin antibodies.

Means for Solving the Problems

As a result of an intensive research, the present inventors found that a lectin bound to haemagglutinin of an influenza virus but did not bind to an antibody, and inferred that when the haemagglutinin is sandwiched between the lectin and an anti-haemagglutinin antibody, only one kind of anti-haemagglutinin antibody is necessary, and an assay system can be constructed in a shorter period of time than a sandwich immunoassay method using two kinds of anti-haemagglutinin antibodies, thereby completing the present invention.

That is, the present invention provides a method for measuring haemagglutinin of an influenza virus by a sandwich immunoassay method, the method comprising sandwiching the haemagglutinin between a lectin which binds to the haemagglutinin but does not bind to an antibody, and an anti-haemagglutinin antibody which undergoes antigen-antibody reaction with the haemagglutinin.

Effect of the Invention

By the present invention, haemagglutinin of an influenza virus can be measured with high accuracy by a sandwich immunoassay method by using one kind of anti-haemagglutinin antibody.

BRIEF DESCRIPTION OF THE DRAWINGS

FIG. 1-2 shows the diagrams similarly to FIG. 1-1.

FIG. 2 shows the relationship between the concentrations of haemagglutinin and absorbances, which was measured by a sandwich immunoassay method in Examples below.

MODE FOR CARRYING OUT THE INVENTION

Figure 1:
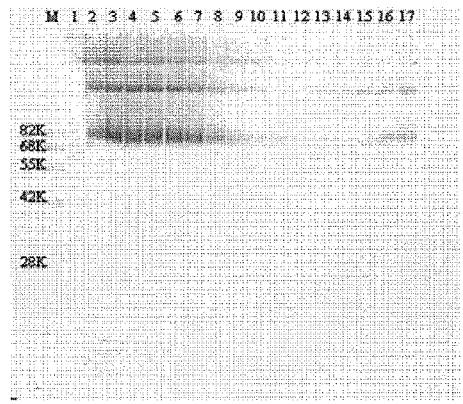
FIG. 1-1 shows Western blotting diagrams illustrating fraction analysis results by sucrose density gradient centrifugation after treating inactivated whole particle virus with each surfactant below. A: no treatment, B: treatment with 1.0% Triton X-100, C: treatment with 1.0% NP-40, D: treatment with 1.0% Tween 80, E: treatment with 1.0% Brij 35, F: treatment with 1.0% CHAPS, G: treatment with 1.0% Zwittergent 3-14, H: treatment with 1.0% CTAB, I: treatment with 0.3% SDS, J: treatment with 4.0 M Urea, K: treatment with 3.0 M of guanidine hydrochloride
Figure 1:
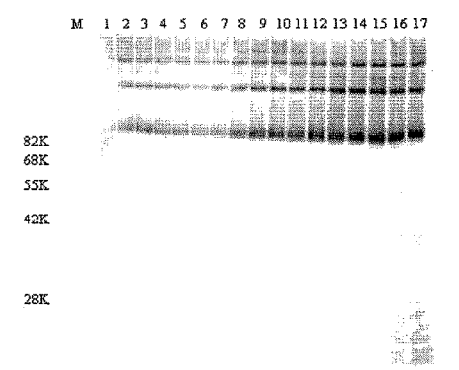
Figure 1:
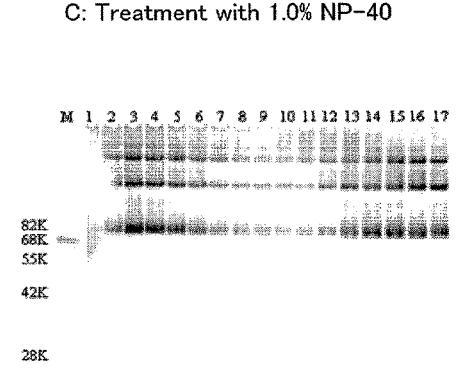
Figure 1:
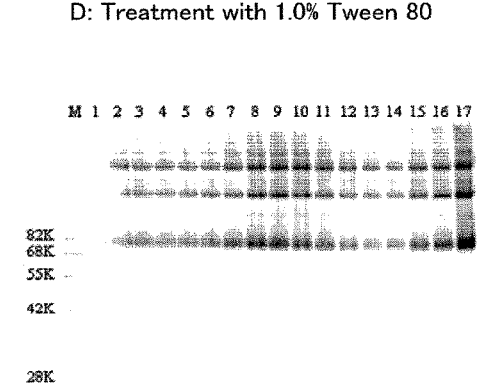

As described above, the method of the present invention is a method for measuring haemagglutinin by a sandwich immunoassay method, the method comprising sandwiching the haemagglutinin between a lectin which binds to the haemagglutinin of an influenza virus (hereinafter referred to as simply "haemagglutinin") but does not bind to an antibody, and an anti-haemagglutinin antibody which undergoes antigen-antibody reaction with the haemagglutinin.

The lectin used in the method of the present invention binds to haemagglutinin. The existence of binding with the haemagglutinin can be confirmed by lectin blot analysis (a labeled lectin is reacted with haemagglutinin transferred on a PVDF membrane to determine whether the label is detected or not) which is specifically described in Reference Example 2 below. The term "does not bind to an antibody" means that the lectin does not bind to an immunoglobulin which belongs to the same species and same class as an immunoglobulin constituting an antibody to be used for the immunoassays (usually, IgG of mouse, rabbit, sheep or the like). The fact that the lectin does not bind to IgG derived from each animal such as mouse, rabbit, sheep or the like can be confirmed by determining whether the absorbance measured by ELISA with HRP-labeled IgG of each animal is less than twice, preferably less than 1.5 times the mean value of those of negative controls (blank) as described in Reference Example 3 below. Preferred examples of the lectin which binds to haemagglutinin but does not bind to an antibody include *Datura stramonium* lectin (DSL), *Erythrina cristagalli* lectin (ECL) and *Ricinus communis* agglutinin (RCA 120). The lectin which binds to haemagglutinin but does not bind to an antibody may be used individually, or two or more of these may be used in combination.

In the method of the present invention, the lectin is preferably immobilized on a solid phase to carry out sandwich immunoassays. As the solid phase, any of those used in well-known sandwich immunoassays such as sandwich ELISA may be employed, and examples thereof include plates, tubes, beads, membranes and gels. The examples of materials of the solid phase include polystyrene, polypropylene, nylon, latex, glass, cross-linked dextrin, agarose, cross-linked agarose and poly acrylamide.

As the method for absorbing the lectin on the solid phase, covalent method, physical adsorption method, ionic bonding method, biochemically specific binding method (for example, a biotinylated lectin is allowed to bind to a solid phase on which streptavidin is immobilized) or the like may be employed. In particular, physical adsorption method and biochemically specific binding method are preferred from the viewpoint of simplicity of the operation.

Examples of the physical adsorption method herein include a method in which a lectin dissolved in a buffer, pH 7 to 9, containing 0.05% Tween 20 (trade name) (for example, Tris-HCl buffer physiological saline, phosphate buffer physiological saline and carbonate buffer) is added to a solid phase (for example, wells of microplate), and the resultant is left to stand at room temperature for about 1 to 2 hours, or at about 4° C. over night to attain the adsorption. As for the biochemically specific binding method, since solid phases on which streptavidin is immobilized (plates, beads or the like) are commercially available, examples thereof include a method in which a lectin dissolved in a buffer, pH 7 to 9, containing 0.05% Tween 20 (trade name) (for example, Tris-HCl buffer physiological saline, phosphate buffer physiological saline and carbonate buffer) is added to the commercially available solid phase on which streptavidin is immobilized, and the resultant is left to stand at room temperature for about 1 to 2 hours, or at about 4° C. over night to attain the adsorption (see Examples below). In any of the physical adsorption method and biochemically specific binding method, although the concentration of lectin to be reacted with the solid phase is not restricted, the final concentration thereof is usually about 10 μg/mL to about 60 μg/mL.

In some cases, surface areas on which lectin was not adsorbed may remain on the surface of the solid phase after the adsorption of the lectin, and in cases where haemagglutinin or other molecular species in a sample are adsorbed to the areas, accurate measurement results may not be obtained. Therefore, it is preferable that a blocking substance is added thereto prior to contacting the sample with the solid phase, to block the areas on which the lectin is not adsorbed. Examples of the blocking substances include serum albumin, casein, milk protein, lactic acid fermentation product, collagen and the decomposed products thereof which can be collected from mammal such as bovine, and those which are commercially available as blocking substances used in immunoassays may also be employed.

The anti-haemagglutinin antibody used in method of the present invention undergoes antigen-antibody reaction with haemagglutinin of an influenza virus, and may be a monoclonal antibody or polyclonal antibody. In the type-specific assay of an influenza virus, an anti-haemagglutinin monoclonal antibody which undergoes antigen-antibody reaction specifically with each type of haemagglutinin is usually employed.

The anti-haemagglutinin antibody is usually labeled. Examples of labeling substances to be used for label include enzymes (peroxidase, alkaline phosphatase, β-galactosidase, luciferase, acetylcholinesterase and the like), isotopes ($^{125}I$, $^{131}I$, $^{3}H$ and the like), fluorescent dyes (luminol, fluorescein isothiocyanate, umbelliferone, 7-amino-4-methylcoumarin-3-acetic acid and the like), chemiluminescent substance, hapten, biotin, avidin (for example, streptavidin and the like), but the labeling substances are not restricted as long as they can be commonly used for labeling proteins. The labeling substance herein includes a substance which per se is not detected directly, like biotin, and which is used in a method in which a material (for example, avidin) capable of specifically binding to the substance, which material is bound to a detectable label, is used in combination.

The above-described method for labeling an antibody can be appropriately selected form known methods suitable to the labeling substance, for example, in the case of labeling enzymes, glutaraldehyde method, periodate crosslinking method, maleimide crosslinking method, carbodiimide method, activated ester method and the like; and in case of label with radioisotopes, chloramine T method, lactoperoxidase method and the like. Since the labeled anti-haemagglutinin antibodies against various types are commercially available, a commercially available one may be employed.

In the method of the present invention, usually, the above-described lectin immobilized on the solid phase, the labeled anti-haemagglutinin antibody and a sample containing haemagglutinin of an influenza virus are reacted, and after washing the solid phase, the labels bound to the solid phase are measured.

The sample to which the method of the present invention is applied may contain influenza virus particles or may be obtained by extracting haemagglutinin from the particles as long as the sample contains haemagglutinin of the influenza virus. It is preferable to extract haemagglutinin because haemagglutinin can be assayed regardless of the manner of existence, whether haemagglutinin exists in virus particles or in a free state, and accuracy of the assay can be increased. The extraction of haemagglutinin can be carried out by using a cationic or an anionic surfactant (both are collectively hereinafter referred to as "ionic surfactant"). Preferred examples of the ionic surfactant include sodium dodecyl sulfate (SDS), lithium dodecyl sulfate (LiDS), hexadecyltrimethylammonium bromide (CTAB), hexadecyltrimethylammonium chloride (CTAC) and hexadecylpyridinium chloride (HPC); and hexadecyltrimethylammonium bromide (CTAB) is particularly preferable. The ionic surfactant can be used individually, and two or more of these can be used in combination.

Although the treatment conditions with the ionic surfactant is not restricted, the ionic surfactant is preferably added to a sample to a final concentration of 0.1 to 2.0%, and the resultant is left to stand or stirred at 37° C. for about 1 to about 2 hours to extract haemagglutinin from virus particles.

The lectin immobilized on the solid phase, a sample and the labeled anti-haemagglutinin antibody may be reacted at the same time; or the lectin immobilized on the solid phase and a sample may be firstly reacted, and after washing the solid phase, the labeled anti-haemagglutinin antibody is reacted therewith; or a sample and the labeled anti-haemagglutinin antibody may be firstly reacted to form an immune complex, and the lectin immobilized on the solid phase is reacted therewith. The reaction can be carried out at room temperature for about 30 minutes to about 120 minutes. The final concentration of haemagglutinin in reaction system is usually about 1 ng/mL to about 1 μg/mL, and the final concentration of the labeled anti-haemagglutinin antibody is usually about 0.2 μg/mL to about 50 μg/mL.

After the reaction, the solid phase is washed, and the labels bound to the solid phase are measured. Examples of washing solutions include buffers to which surfactants such as Tween (trade name) type surfactant are added (for example, phosphate buffer, phosphate buffer physiological saline, Tris-HCl buffer, Tris-HCl buffer physiological saline). The method for detecting the labeled substance are different depending on the labeling substance to be used, and in the case of using biotin as a labeling substance, examples thereof include a method in which an enzyme such as peroxidase is allowed to be bound to a complex containing biotin as a labeling substance through streptavidin or the like, a chromogenic substance such as tetramethylbenzidine and hydrogen peroxide solution as substrates of the enzyme are added thereto measure the degree of coloring of the product caused by enzyme reaction based on the change in absorbance. In the case of using a fluorescent substance or a chemiluminescence substance as a labeling substance, examples thereof include a method for measuring fluorescence or luminescence of the solution obtained after the reaction.

Instead of the labeled anti-haemagglutinin antibody, a non-labeled anti-haemagglutinin antibody is reacted therewith, a labeled anti-immunoglobulin antibody is further reacted therewith, and after washing, the labels bound to the solid phase may be measured (indirect antibody technique). Since the number of antigen-antibody reaction is increased by one time in the indirect antibody technique, when quick test is necessary, the above-described direct technique using a labeled anti-haemagglutinin antibody is preferred.

In the measuring method of the present invention, the relationship between the concentration of haemagglutinin and the detection results of the labeled substances is plotted using a standard solution containing a known concentration of haemagglutinin to prepare a calibration curve, and the concentration of haemagglutinin in a sample may be quantified by using the detection result of the sample having unknown concentration and the above-described calibration curve.

An preferable embodiment of the measuring method of the present invention will now be described. Firstly, the lectin is adsorbed (coated) on the solid phase. The preferable adsorption method is as described above.

After the adsorption, it is preferred to block the areas to which the lectin is not adsorbed by adding a buffer containing a blocking substance such as skim milk, and leaving the resultant to stand at room temperature for about 30 minutes to about 2 hours.

In cases where the haemagglutinin in a sample exists in virus particles, CTAB is added to the sample to a final concentration of 0.1 to 2.0%, and the resultant is left to stand or stirred at 37° C. for about 1 to about 2 hours to extract the haemagglutinin form the virus particles.

Then, a sample or a sample obtained by carrying out the extraction treatment of haemagglutinin is added to the solid phase on which the lectin was adsorbed, and the resultant is left to stand or stirred, for example, at room temperature for an appropriate time of 30 to 120 minutes to bind the haemagglutinin to the lectin.

Thereafter, the solid phase to which this complex is bound is washed with a washing solution such as a buffer containing Tween type surfactant or the like (for example, Tris-HCl buffer physiological saline, phosphate buffer physiological saline or the like). Further, the anti-haemagglutinin antibody labeled with a labeling substance; or the anti-haemagglutinin antibody and the anti-anti-haemagglutinin antibody labeled with a labeling substance is(are) added to the solid phase, and the resultant is left to stand or stirred, for example, at room temperature for 30 to 120 minutes to bind the anti-haemagglutinin antibody (or the anti-haemagglutinin antibody-anti-anti-haemagglutinin antibody) to the haemagglutinin. By this procedure, the complex composed of the solid phase-lectin-haemagglutinin-anti-haemagglutinin antibody (or the solid phase-lectin-haemagglutinin-anti-haemagglutinin antibody-anti-anti-haemagglutinin antibody) is allowed to be formed. Next, the labeled substance of the complex is detected to measure the haemagglutinin.

The relationship between the concentrations of haemagglutinin standards and the detection results of the labeled substances (for example, absorbances) is plotted to prepare a calibration curve, and the concentration of haemagglutinin in an unknown sample may be quantified by using the detection result of the unknown sample and the above-described calibration curve.

EXAMPLES

The present invention will now be described more concretely by way of Examples thereof; however, the present invention is not restricted at all to the following Examples.

Reference Example 1

Study on Surfactant for Extracting Haemagglutinin

To inactivated whole particle virus of A/Brisbane/59/2007 strain, which was amplified in an embryonated egg, and purified and inactivated by ultrafiltration, sucrose density gradient centrifugation and 3-propiolactone, Triton X-100 (trade name, produced by Sigma-Aldrich Japan), NP-40 (trade name, produced by Nacalai Tesque), Tween 80 (trade name, produced by Wako Pure Chemicals), Brij 35 (trade name, produced by Wako Pure Chemicals), CHAPS (trade name, produced by Dojindo Laboratories), Zwittergent 3-14 (trade name, produced by Calbiochem) and CTAB (produced by Wako Pure Chemicals) were each added to a final concentration of 1.0%. SDS was added to a final concentration of 0.3%; and Urea (produced by M P Bio Japan) and guanidine hydrochloride (produced by M P Bio Japan) were added to a final concentration of 4.0 M and 3.0 M respectively. The resultant was left to stand at 37° C. for 60 minutes to allow reaction. Sucrose was added to the reaction solution to a final concentration of 20%, and the resultant was fractionated into 17 fractions by sucrose density gradient centrifugation having a fraction density of 20 to 50 w/w %. Equal amounts of each fraction solution and a sample buffer for SDS-PAGE (8% SDS, 40% glycerol/250 mM Tris-HCl Buffer, pH 6.8) were mixed and the resultant was left to stand at 100° C. for 5 minutes to allow reaction. The reaction solution was electrophoresed on 12.5% polyacrylamide gel (e-PAGEL produced by ATTO), and transferred to a PVDF membrane with a semidry transfer apparatus (produced by ATTO). The PVDF membrane after the transfer was immersed in 75 mL of blocking buffer (TBS containing 10% skim milk), and masking reaction was carried out at room temperature for 4 hours. After the reaction, the PVDF membrane was washed with an appropriate amount of TBS three times, and the PVDF membrane was then immersed in anti-HA antibody solution (antiserum for SRD (Single radial immunodiffusion)), followed by reaction at 4° C. for about 16 hours (reaction with primary antibody). After the reaction with primary antibody, the PVDF membrane was washed with TBS containing Tween 20 (trade name) five times, and HRP-labeled anti-sheep antibody (produced by Bethyl) solution was added thereto, followed by reaction at room temperature for 60 minutes (reaction with secondary antibody). After the reaction with secondary antibody, the PVDF membrane was washed with TBS containing Tween 20 (trade name) five times, and the haemagglutinin was detected by Super Signal West Pico Chemiluminescent Substrate (trade name, produced by Thermo Scientific). For the detection, LAS-3000 (trade name, produced by GE Healthcare) was used.

By this, as shown in FIG. 1, in case of the untreated inactivated whole particle virus or in case of the treatment with Urea or guanidine hydrochloride which is a protein-denaturant, the haemagglutinin was detected only in high-density regions; and in case of the treatments with Triton X-100 (trade name), NP-40 (trade name), Tween 80 (trade name) and Brij 35 (trade name) as non-ionic surfactants and in case of the treatments with CHAPS (trade name) and Zwittergent 3-14 (trade name) as amphoteric surfactants, the haemagglutinin was detected in various density regions from high-density to low-density. On the other hand, since the treatment with CTAB or SDS as ionic surfactants causes the bands of haemagglutinin to transfer to low-density regions, it can be seen that the treatment with ionic surfactants is most suitable to the solubilization and extraction treatment of the haemagglutinin.

Reference Example 2

Binding Between Various Lectins and Haemagglutinin

In MDCK cells and an embryonated egg, six virus solutions each containing a strain of A/California/7/2009 (H1N1), A/Brisbane/59/2007 (H1N1), A/Victoria/210/2009 (H3N2), A/Uruguay/716/2007 (H3N2), B/Brisbane/60/2008 (B type Victoria lineage) and B/Florida/4/2006 (B type Yamagata lineage) respectively were prepared. Equal amounts of the prepared virus and a sample buffer for SDS-PAGE (8% SDS, 40% glycerol/250 mM Tris-HCl Buffer, pH 6.8) were mixed and the resultant was left to stand at 100° C. for 5 minutes to allow reaction. The reaction solution was electrophoresed on 12.5% polyacrylamide gel (e-PAGEL produced by ATTO), and transferred to a PVDF membrane with a semidry transfer apparatus (produced by ATTO). The PVDF membrane after the transfer was immersed in 75 mL of blocking buffer (TBS containing 10% skim milk), and masking reaction was carried out at room temperature for 4 hours. After the reaction, the PVDF membrane was washed with an appropriate amount of TBS three times and the reaction with various biotinylated lectins (produced by VECTOR LABORATORIES) was carried out at room temperature for 4 hours. After the reaction with lectin, the PVDF membrane was washed with TBS containing Tween 20 (trade name) five times, and HRP labelled-streptavidin (produced by Thermo Scientific) solution was added thereto, followed by reaction at room temperature for 60 minutes. After the reaction, the PVDF membrane was washed with TBS containing Tween 20 (trade name) five times, and the complex composed of haemagglutinin and the lectin was detected by Super Signal West Pico Chemiluminescent Substrate (trade name, produced by Thermo Scientific). For the detection, LAS-3000 (trade name, produced by E Healthcare) was used.

As a result, it was confirmed that any of RCA 120, DSL and ECL can bind to haemagglutinin derived from viruses which were prepared by using both MDCK cells and an embryonated egg as a base for expression.

Reference Example 3

Binding Between Various Lectins and IgG

To streptavidin-coated microplate (produced by Nunc), each biotinylated lectin, which was diluted with 0.05% Tween 20 (trade name)/Tris-HCl buffer physiological saline (TBST) to a final concentration of 30 µg/mL, was added in an amount of 100 µL/well, and the resultant was reacted at 25° C. for 2 hours. After the reaction with the lectin, each well was washed with 300 µL of Wash buffer (TBST) five times. Then, 300 µL of 2.5% skim milk/TBST was added to each well to carry out blocking at 25° C. for 1 hour, and each well was then washed with 300 µL of Wash buffer five times. A HRP-labeled IgG antibody diluted with 0.5% skim milk/TBST or 0.5% BSA/TBST (mouse antibody: Mouse Anti-Rabbit IgG Secondary Antibody (H+L), HRP Conjugated, produced by BioSS; rabbit antibody: Sheep IgG-heavy and light chain antibody, produced by Bethyl Laboratories; sheep antibody: Rabbit IgG-heavy and light chain antibody, produced by Bethyl Laboratories) was added to each well in an amount of 100 µL, and the resultant was reacted at 25° C. for 1 hour. After the antibody reaction, each well was washed with 300 µL of Wash buffer five times, and 200 µl, of TMB solution (produced by Wako Pure Chemicals) was added to each well to allow reaction at 25° C. for 20 minutes. Then, 50 µL of 1 mol/L sulfuric acid (produced by Wako Pure Chemicals) was added to each well to stop the reaction. Thereafter, the absorbances were measured at 450 nm.

The results are shown in Table 1. As shown in Table 1, it can be seen that in any of RCA 120, DSL and ECL, the absorbances measured after being subjected to the reaction with mouse, rabbit and sheep IgGs are less than twice of the absorbances in the negative control (blank), which indicates that RCA 120, DSL and ECL do not react with mouse, rabbit and sheep IgGs.

Since it is confirmed in the Reference Example 2 that any of RCA 120, DSL and ECL bind to haemagglutinin, any of these lectins were thought to measure haemagglutinin by sandwich immunoassays.

TABLE 1

| Lectin | BLANK | | | | Mouse IgG | | | Rabbit IgG | | | Sheep IgG | | |
|---|---|---|---|---|---|---|---|---|---|---|---|---|---|
| | 1 | 2 | 3 | mean | 1 | 2 | 3 | 1 | 2 | 3 | 1 | 2 | 3 |
| RCA120 | 0.057 | 0.051 | 0.055 | 0.054 | 0.065 | 0.072 | 0.070 | 0.079 | 0.079 | 0.077 | 0.065 | 0.063 | 0.067 |
| DSL | 0.046 | 0.047 | 0.050 | 0.048 | 0.055 | 0.061 | 0.061 | 0.055 | 0.056 | 0.058 | 0.054 | 0.053 | 0.052 |
| ECL | 0.049 | 0.051 | 0.047 | 0.049 | 0.053 | 0.061 | 0.058 | 0.056 | 0.058 | 0.057 | 0.052 | 0.055 | 0.051 |

Example 1

Sandwich Immunoassay

To a vial containing a standardized antigen for SRD Test purchased from NIBSC (The National Institute for Biological Standards and Control), 1 mL of water was added, and after leaving the vial to stand for 5 minutes, the solution was well stirred (50 µg HA/mL). A NIBSC standard product (50 µg HA/mL) in an amount of 50 µL and 1.0% CTAB in an amount of 50 µL were mixed and stirred well (25 µg HA/mL), followed by leaving the mixture to stand at 37° C. for 2 hours. Then, the mixture was diluted 10-fold to prepare a 2.5 µg HA/mL of haemagglutinin solution. This standard solution was diluted to prepare 3.13, 6.25, 12.5, 25, 50, 100 and 250 ng HA/mL of haemagglutinin solutions.

To streptavidin-coated microplate (produced by Nunc), each biotinylated lectin diluted with 0.05% Tween 20 (trade name)/Tris-HCl buffer physiological saline (TBST) was added to a final concentration of 30 µg/mL in an amount of 100 µL/well, and the resultant was reacted at 25° C. for 2 hours. After the reaction with the lectin, each well was washed with 300 µL of Wash buffer (TBST) five times. Then, 300 µL of 2.5% skim milk/TBST was added to each well to carry out blocking at 25° C. for 1 hour, and each well was then washed with 300 µL of Wash buffer five times. The prepared haemagglutinin solution having each concentration was added to each well in an amount of 100 µL, and the resultant was reacted at 25° C. for 1 hour. After the reaction, each well was washed with 300 µL of Wash buffer five times, and a HRP-labeled anti-haemagglutinin antibody (attached with 2009H1N1 Influenza (Swine Flu) Haemagglutinin ELISA kit, produced by Sino Biological) solution diluted with 0.5% skim milk/TBST to a final concentration of 2 µg/mL was added to each well in an amount of 100 µL, and the resultant was reacted at 25° C. for 1 hour. After the reaction with the anti-haemagglutinin antibody, each well was washed with 300 µL of Wash buffer five times, and 200 µL of TMB solution (produced by Wako Pure Chemicals) was added to each well to allow reaction at 25° C. for 20 minutes. Then, 50 µL of 1 mol/L sulfuric acid (produced by Wako Pure Chemicals) was added to each well to stop the reaction. Thereafter, the absorbances were measured at 450 nm.

Figure 2:
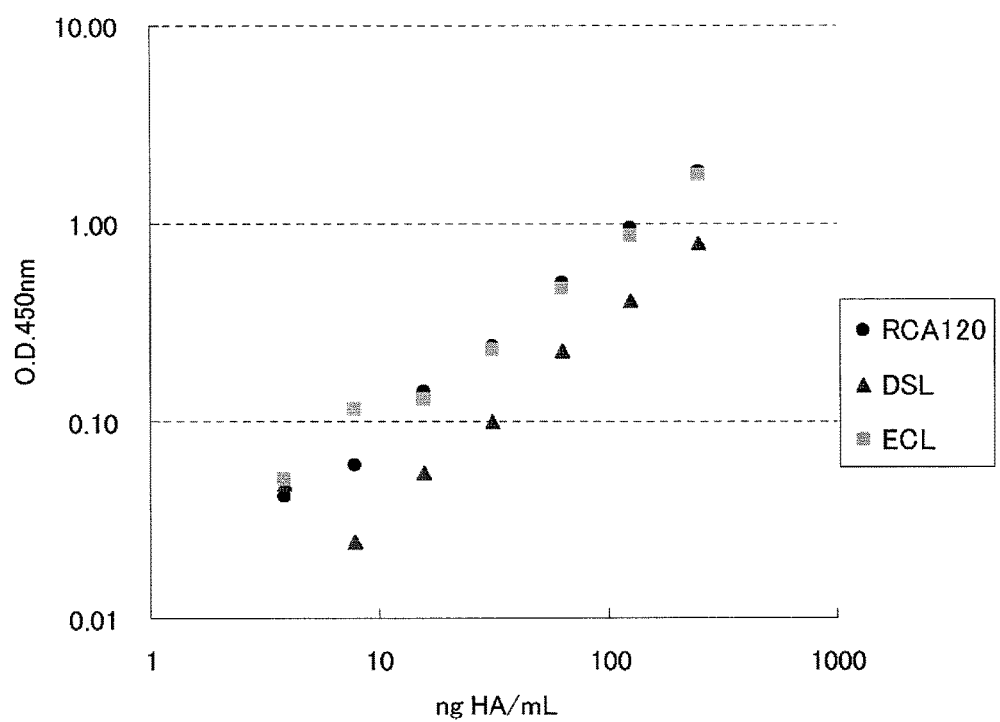

Although Table 2 and FIG. 2 show the measurement results of haemagglutinin by ELISA using RCA 120, DSL and ECL, it was confirmed that there is a good correlation between haemagglutinin (HA) concentrations and the absorbances in any of these lectins. Therefore, the method for measuring haemagglutinin with high sensitivity can be attained by using the lectin bound to haemagglutinin and one kind of anti-haemagglutinin antibody.

TABLE 2

| HA concentration (ng/mL) | RCA120 | DSL | ECL |
| --- | --- | --- | --- |
| 250 | 1.936 | 0.850 | 1.808 |
| 125 | 1.040 | 0.462 | 0.916 |
| 62.5 | 0.589 | 0.285 | 0.506 |
| 31.3 | 0.322 | 0.158 | 0.272 |
| 15.6 | 0.223 | 0.112 | 0.170 |
| 7.81 | 0.144 | 0.083 | 0.158 |
| 3.91 | 0.125 | 0.106 | 0.093 |
| BLANK | 0.084 | 0.058 | 0.042 |

Example 2

Confirmation of Correlation with Measured Values of SRD Test

To each vial containing standard influenza HA antigen (for single radial immunodiffusion test, National Institute of Infectious Diseases) of A/California/07/2009 (X-179A), ANictoria/361/2011 (IVR-165) or B/Wisconsin/01/2010 (BX-41A), 1 mL of water was added, and after leaving the vial to stand for 5 minutes, the solution was well stirred. A standard influenza HA antigen solution in an amount of 50 µL and 1.0% CTAB in an amount of 50 µL were mixed and the mixture was stirred well, followed by leaving the mixture to stand at 37° C. for 2 hours. Then, the mixture was diluted 10-fold to prepare a haemagglutinin solution. This standard solution was diluted to prepare 1.95, 3.91, 7.81, 31.3, 62.5 and 125 ng HA/mL of haemagglutinin solutions to obtain standard solutions for a calibration curve. The solutions from the preparation step (A/California/07/2009 (X-179A) strain, ANictoria/361/2011 (IVR-165) strain and B/Wisconsin/01/2010 (BX-41A) strain) each of which HA concentration was determined by single radial immunodiffusion test (SRD Test) were also treated with CTAB and diluted in the same manner as the standard solutions for a calibration curve to prepare test samples.

To streptavidin-coated microplate (produced by Nunc), biotinylated ECL diluted with 0.05% Tween 20 (trade name)/Tris-HCl buffer physiological saline (TBST) to a final concentration of 30 µg/mL was added in an amount of 100 µL/well, and the resultant was reacted at 25° C. for 2 hours. After the reaction with the lectin, each well was washed with 300 µL of Wash buffer (TBST) five times. Then, 300 µL of 2.5% skim milk/TBST was added to each well to carry out blocking at 25° C. for 1 hour, and each well was then washed with 300 µL of Wash buffer five times. The prepared standard solutions for a calibration curve and test samples were added to each well in an amount of 100 µL, and the resultant was reacted at 25° C. for 2 hour. After the reaction, each well was washed with 300 µL of Wash buffer five times, and 100 µL of Influenza antiserum reagent (for single radial immunodiffusion test, National Institute of Infectious Diseases) solution of each strain diluted 2500-fold with 0.5% skim milk/TBST was added as an anti-haemagglutinin antibody to each well to allow reaction at 25° C. for 1 hour. After the reaction with the anti-haemagglutinin antibody, each well was washed with 300 µL of Wash buffer five times. A HRP-labeled anti-sheep IgG antibody (Bethyl Laboratories) diluted 2500-fold with 0.5% skim milk/TBST was added to each well in an amount of 100 and the resultant was reacted at 25° C. for 1 hour. After the reaction with the anti-sheep IgG antibody, 200 µL of TMB solution (produced by Wako Pure Chemicals) was added to each well to allow reaction at 25° C. for 20 minutes, and 50 µL of 1 mol/L sulfuric acid (produced by Wako Pure Chemicals) was then added to each well to stop the reaction. Thereafter, the absorbances were measured at 450 nm.

Table 3, Table 4 and Table 5 show measurement results of SRD Test, measurement results of ELISA using lectin bound to haemagglutinin, and ratios of the measured values of ELISA to the measured values of SRD Test, for subtype A/H1N1 (A/California/07/2009 X-179A), subtype A/H3N2 (A/Victoria/361/2011 IVR-165) and type B (B/Wisconsin/01/2010 BX-41A). As shown in Tables, ratios of the measured values of ELISA to the measured values of SRD Test were 92.2 to 111% for subtype A/H1N1, 96.9% to 132% for subtype A/H3N2 and 80.4 to 91.6% for type B, and good correlations could be confirmed. Therefore, by the ELISA using the lectin bound to haemagglutinin of the present invention, the measured values correlating with the results of SRD Test which is a potency test of vaccine can be obtained.

TABLE 3

A/H1N1: A/California/07/2009 (X-179A)

| Sample | ELISA (ugHA/mL) | SRD (ugHA/mL) | Ratio (%) (ELISA/SRD) |
|---|---|---|---|
| H1-1 | 458 | 412 | 111 |
| H1-2 | 441 | 425 | 104 |
| H1-3 | 451 | 436 | 103 |
| H1-4 | 445 | 430 | 103 |
| H1-5 | 425 | 416 | 102 |
| H1-6 | 432 | 405 | 107 |
| H1-7 | 422 | 433 | 97.5 |
| H1-8 | 389 | 422 | 92.2 |
| H1-9 | 411 | 418 | 98.3 |
| H1-10 | 421 | 410 | 103 |

TABLE 4

A/H3N2: A/Victoria/361/2011 (IVR-165)

| Sample | ELISA (ugHA/mL) | SRD (ugHA/mL) | Ratio (%) (ELISA/SRD) |
|---|---|---|---|
| H3-1 | 467 | 361 | 129 |
| H3-2 | 482 | 398 | 121 |
| H3-3 | 440 | 370 | 119 |
| H3-4 | 435 | 372 | 117 |
| H3-5 | 411 | 366 | 112 |
| H3-6 | 436 | 387 | 113 |
| H3-7 | 475 | 361 | 132 |
| H3-8 | 442 | 386 | 115 |
| H3-9 | 428 | 377 | 114 |
| H3-10 | 373 | 384 | 97.1 |

TABLE 5

B: B/Wisconsin/01/2010 (BX-41A)

| Sample | ELISA (ugHA/mL) | SRD (ugHA/mL) | Ratio (%) (ELISA/SRD) |
|---|---|---|---|
| B-1 | 395 | 431 | 91.6 |
| B-2 | 362 | 423 | 85.6 |
| B-3 | 365 | 412 | 88.6 |
| B-4 | 353 | 422 | 83.6 |
| B-5 | 353 | 439 | 80.4 |
| B-6 | 375 | 451 | 83.1 |
| B-7 | 391 | 446 | 87.7 |
| B-8 | 365 | 437 | 83.5 |
| B-9 | 384 | 461 | 83.3 |
| B-10 | 363 | 436 | 83.3 |

The invention claimed is:

1. A method for measuring haemagglutinin of an influenza virus by a sandwich immunoassay method, said method comprising:
   extracting haemagglutinin from a sample containing the influenza virus by adding a cationic or anionic surfactant;
   combining the extracted haemagglutinin with at least one lectin immobilized on a solid support and with a labeled anti-haemagglutinin antibody that undergoes antigen-antibody reaction with the haemagglutinin; and
   measuring the haemagglutinin by sandwich immunoassay, wherein detection of the presence of haemagglutinin indicates the presence of influenza virus,
   wherein the at least one lectin binds the haemagglutinin, but does not bind the anti-haemagglutinin antibody, and
   wherein the at least one lectin is *Datura stramonium* lectin, and
   wherein the cationic and anionic surfactant is at least one selected from the group consisting of sodium dodecyl sulfate, lithium dodecyl sulfate, hexadecyltrimethylammonium bromide, hecadecyltrimethylammonium chloride and hexadecylpyridinium chloride.

2. The method of claim 1, wherein the at least one lectin is immobilized on a solid phase and the anti-haemagglutinin antibody is labeled, said method comprising measuring the labeled antibody which is bound to the solid phase through the at least one lectin and the haemagglutinin.

3. The method of claim 1, wherein the surfactant is hexadecyltrimethylammonium bromide.

4. The method of claim 1, wherein the cationic or the anionic surfactant is added to the sample to a final concentration of 0.1 to 2.0%.

5. The method of claim 1, wherein the cationic or anionic surfactant is at least one selected from the group consisting of lithium dodecyl sulfate, hexadecyltrimethylammonium bromide, hexadecyltrimethylammonium chloride and hexadecylpyridinium chloride.

6. The method of claim 1, wherein the lectin is a biotinylated lectin.

7. A method for measuring haemagglutinin of an influenza virus by a sandwich immunoassay method, said method comprising:
   extracting haemagglutinin from a sample containing the influenza virus by adding a cationic or anionic surfactant;
   combining the extracted haemagglutinin with at two or more lectins immobilized on a solid support and with a labeled anti-haemagglutinin antibody that undergoes antigen-antibody reaction with the haemagglutinin; and
   measuring the haemagglutinin by sandwich immunoassay, wherein detection of the presence of haemagglutinin indicates the presence of influenza virus,
   wherein the two or more lectins bind the haemagglutinin, but do not bind the anti-haemagglutinin antibody, and
   wherein at least one lectin is *Datura stramonium* lectin, and
   wherein the cationic and anionic surfactant is at least one selected from the group consisting of sodium dodecyl sulfate, lithium dodecyl sulfate, hexadecyltrimethylammonium bromide, hecadecyltrimethylammonium chloride and hexadecylpyridinium chloride.

8. The method of claim 7, wherein at least one lectin is *Datura stramonium* and second lectin is *Erythrina cristagalli* lectin (ECL) or *Ricinius communis* agglutinin (RCA 120).

* * * * *